United States Patent [19]
Cornelius et al.

[11] Patent Number: 5,382,234
[45] Date of Patent: Jan. 17, 1995

[54] OVER-THE-WIRE BALLOON CATHETER

[75] Inventors: Richard G. Cornelius, Golden Valley; Larry A. Walter, Minneapolis; Douglas C. Lee, Maple Grove; Frank A. Musbach, St. Paul, all of Minn.

[73] Assignee: SciMed Life Systems, Inc., Maple Grove, Minn.

[21] Appl. No.: 45,017

[22] Filed: Apr. 8, 1993

[51] Int. Cl.⁶ .............................................. A61M 29/00
[52] U.S. Cl. .................................... 604/96; 604/280; 604/282; 606/194
[58] Field of Search .................. 604/93, 95, 96, 97, 604/98, 99, 101, 102, 103, 104; 606/191, 194, 192, 195

[56] References Cited

U.S. PATENT DOCUMENTS

| | | |
|---|---|---|
| B1 4,024,873 | 9/1984 | Antoshkiw et al. . |
| B1 4,323,071 | 5/1990 | Simpson et al. . |
| B1 4,762,129 | 7/1991 | Bonzel . |
| 3,817,809 | 6/1974 | Dereniuk . |
| 4,024,873 | 5/1977 | Antoshkiw et al. . |
| 4,195,637 | 4/1980 | Grüntzig et al. . |
| 4,323,071 | 4/1982 | Simpson et al. . |
| 4,405,313 | 9/1983 | Sisley et al. . |
| 4,406,656 | 9/1983 | Hattler et al. . |
| 4,456,000 | 6/1984 | Schjeldahl et al. . |
| 4,496,345 | 1/1985 | Hasson . |
| 4,573,470 | 3/1986 | Samson et al. . |
| 4,597,755 | 7/1986 | Samson et al. . |
| 4,616,653 | 10/1986 | Samson et al. . |
| 4,646,742 | 3/1987 | Packard et al. . |
| 4,719,924 | 1/1988 | Crittenden et al. . |
| 4,729,914 | 3/1988 | Kliment et al. . |
| 4,739,768 | 4/1988 | Engelson . |
| 4,744,366 | 5/1988 | Jang ...................................... 604/101 |
| 4,748,982 | 6/1988 | Horzewski et al. . |
| 4,762,129 | 8/1988 | Bonzel . |
| 4,775,371 | 10/1988 | Mueller, Jr. . |
| 4,782,834 | 11/1988 | McGuire et al. ...................... 604/96 |
| 4,798,586 | 1/1989 | Stevens . |
| 4,819,751 | 1/1989 | Shimada et al. . |
| 4,820,349 | 4/1989 | Saab . |
| 4,846,174 | 7/1989 | Willard et al. . |
| 4,877,031 | 10/1989 | Conway et al. . |
| 4,888,573 | 12/1989 | Wijay . |
| 4,896,670 | 12/1989 | Crittenden . |
| 4,906,241 | 3/1990 | Noddin et al. . |
| 4,911,163 | 3/1990 | Fina ...................................... 604/101 |
| 4,917,088 | 4/1990 | Crittenden . |
| 4,921,483 | 5/1990 | Wijay et al. . |
| 4,932,413 | 6/1990 | Shockey et al. . |
| 4,943,278 | 7/1990 | Euteneuer . |
| 4,946,466 | 8/1990 | Pinchuk et al. . |
| 4,947,864 | 8/1990 | Shockey et al. . |
| 4,960,410 | 10/1990 | Pinchuk . |
| 4,964,409 | 10/1990 | Tremulis . |
| 4,976,690 | 12/1990 | Solar et al. . |
| 4,981,478 | 1/1991 | Evard et al. . |
| 4,983,167 | 1/1991 | Sahota et al. . |
| 4,994,032 | 2/1991 | Sugiyama et al. . |
| 4,998,917 | 3/1991 | Gaiser et al. ........................... 604/96 |

(List continued on next page.)

FOREIGN PATENT DOCUMENTS

| | | |
|---|---|---|
| 0279958 | 8/1988 | European Pat. Off. . |
| 2130093 | 5/1984 | United Kingdom . |
| 8902763 | 4/1989 | WIPO . |

Primary Examiner—C. Fred Rosenbaum
Assistant Examiner—Perry E. Van Over
Attorney, Agent, or Firm—Nawrocki, Rooney & Sivertson

[57] ABSTRACT

An over-the-wire catheter and method of making such a catheter having a first tubular member defining a first lumen and a second tubular member defining a second lumen joined to and coextending with the exterior of the first tubular member to define a catheter shaft. The first and second tubular members being formed independently of one another or of different materials. A balloon is joined to the distal end of the catheter shaft where it is in fluid communication with the first lumen. A flexibility control member may be joined to and coextend with the first and second tubular members.

13 Claims, 2 Drawing Sheets

U.S. PATENT DOCUMENTS

| | | |
|---|---|---|
| 4,998,923 | 3/1991 | Samson et al. . |
| 5,002,532 | 3/1991 | Gaiser et al. . |
| 5,015,230 | 5/1991 | Martin et al. . |
| 5,045,061 | 9/1991 | Seifert et al. . |
| 5,047,045 | 9/1991 | Arney et al. . |
| 5,049,130 | 9/1991 | Powell ................................ 604/96 |
| 5,059,170 | 10/1991 | Cameron . |
| 5,059,177 | 10/1991 | Towne et al. ..................... 606/194 |
| 5,074,845 | 12/1991 | Miraki et al. ..................... 604/101 |
| 5,100,381 | 3/1992 | Burns . |
| 5,141,494 | 8/1992 | Danforth . |
| 5,147,377 | 9/1992 | Sahota . |
| 5,176,637 | 1/1993 | Sagoe . |
| 5,207,648 | 5/1993 | Gross ................................. 604/93 |
| 5,209,741 | 5/1993 | Spaeth . |
| 5,226,880 | 7/1993 | Martin . |
| 5,232,445 | 8/1993 | Bonzel . |
| 5,238,005 | 8/1993 | Imran ................................. 604/95 |
| 5,242,396 | 9/1993 | Evard . |

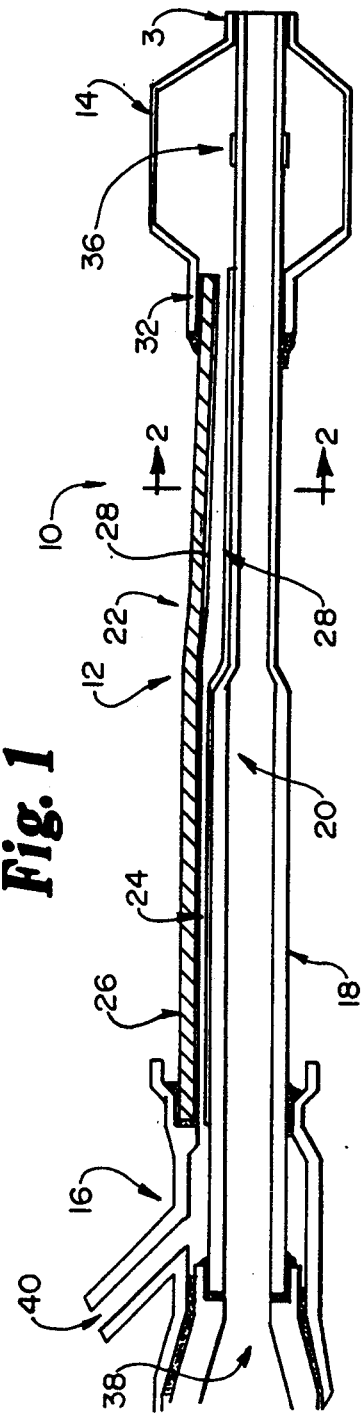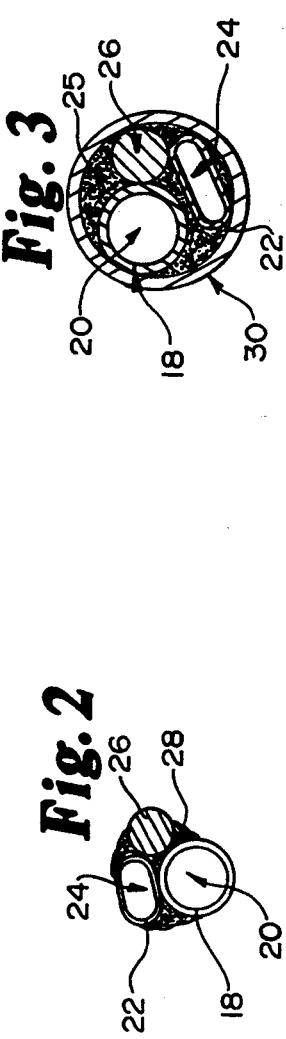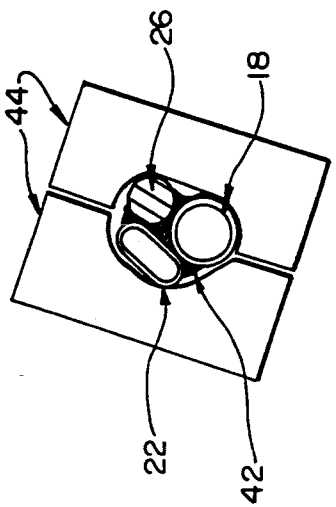

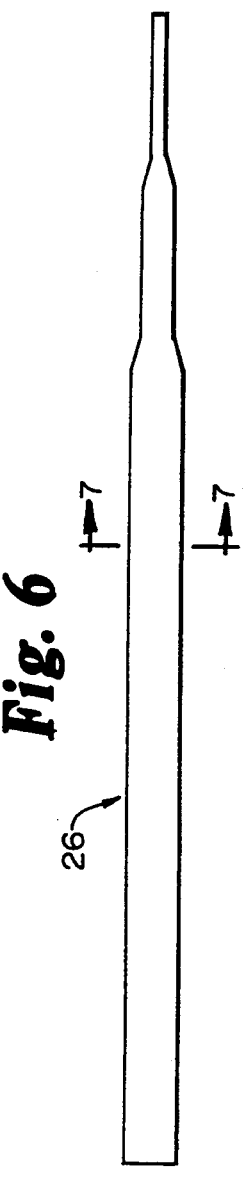
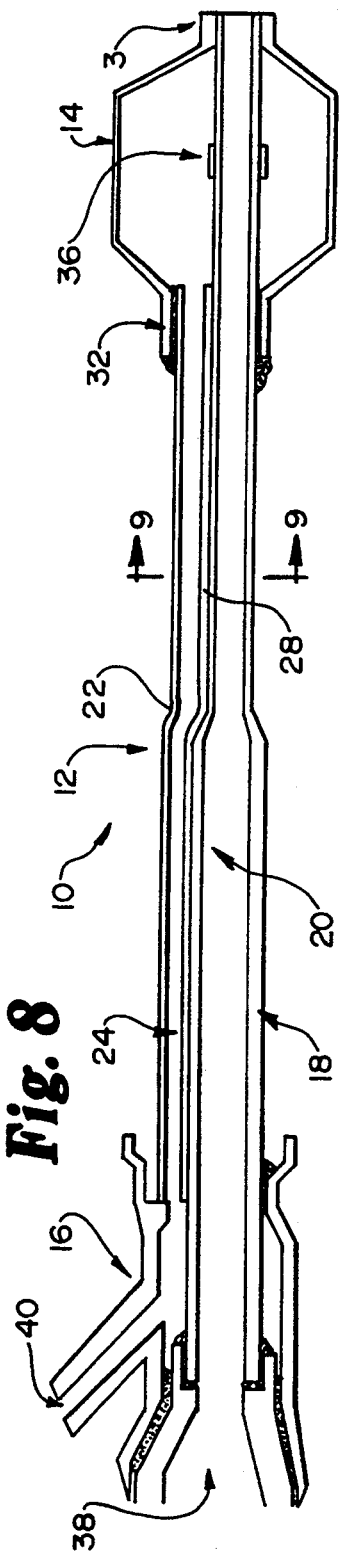
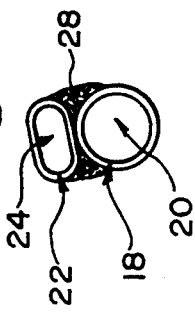
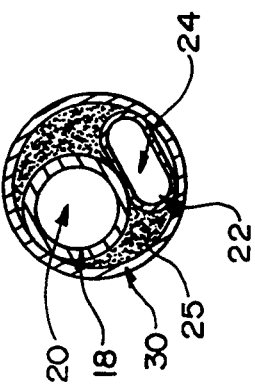

OVER-THE-WIRE BALLOON CATHETER

BACKGROUND OF THE INVENTION

Angioplasty procedures have gained wide acceptance in recent years as efficient and effective methods for treating types of vascular disease. In particular, angioplasty is widely used for opening stenoses in the coronary arteries, although it is also used for the treatment of stenoses in other parts of the vascular system.

One form of angioplasty makes use of a dilation catheter which has an inflatable balloon at its distal end. Typically, in coronary procedures, a hollow guide catheter is used in guiding the dilation catheter through the vascular system to a position near the stenosis. Using fluoroscopy, the physician guides the dilation catheter the remaining distance through the vascular system until the balloon is positioned to cross the stenosis. The balloon is then inflated by supplying fluid under pressure through an inflation lumen in the catheter to the balloon. The inflation of the balloon causes a widening of the lumen of the artery to reestablish acceptable blood flow through the artery. In procedures in the peripheral vessels (i.e., vessels other than coronary vessels) the guide catheter may not always be used.

One commonly used type of dilation catheter is referred to as an "over-the-wire" catheter. An over-the-wire catheter is one in which a guidewire lumen is provided in the catheter so that a guidewire can be used to establish the path through the stenoses. The dilation catheter can then be advanced over the guidewire until the balloon on the catheter is positioned within the stenoses. Two commonly used types of over-the-wire catheters are referred to as coaxial catheters and dual or multiple lumen catheters. A coaxial catheter is one in which the guidewire lumen is formed by an inner tube and the inflation lumen is formed between the exterior surface of the inner tube and the inner surface of a coaxially disposed outer tube. A dual or multiple lumen catheter is one in which the guidewire lumen and inflation lumen or lumens are formed of the same material and adjacent to one another in a single tube.

Preferably a dilation catheter will have several performance characteristics. First, there has been a continuing effort to reduce the balloon profile and shaft size of the dilation catheter so that the catheter can reach and can cross a very tight stenosis and also be used in smaller diameter guide catheters. Portions of the dilation catheter must also be sufficiently flexible to pass through tight curvatures especially in the coronary arteries. The ability of the catheter to bend and advance through the vasculature is commonly referred to as the "trackability" of the catheter. A further requirement of a dilation catheter is its "pushability". This involves the transmission of longitudinal forces along the catheter from its proximal end to its distal end so that a physician can push the catheter through the vasculature system and the stenoses. The catheter should be both relatively trackable and pushable. Another requirement of a dilation catheter is a rapid inflation and deflation rate. The inflation lumen of the catheter should be sufficiently sized to allow the balloon to be quickly inflated and deflated. Another requirement is good wire movement. The wire lumen should have a combination of diameter and material which minimizes friction against the guidewire.

It is desirable to design and construct an over-the wire catheter for which each of the above described performance characteristics are defined predominantly by one component. This allows a performance characteristic of the catheter to be altered from one model to another by changing one component without having to change the others. This isolation of one characteristic to one component also allows the size and material of the components to be optimized for the performance characteristic it defines without making compromises for other characteristics effected.

For example, with reference to the dual or multiple lumen catheter, the design choices for the components are limited. Due to the construction of the catheter, the guidewire lumen and the inflation lumen are formed of the same material. This creates a disadvantage in that while a material may be selected to enhance one characteristic of the catheter such as its trackability, another characteristic such as the wire movement provided in the guidewire lumen may be compromised. With reference to the coaxial catheter, the design choices are also limited. The dimension of the inner tube is determined by the size of the guidewire to be used with the catheter. The dimension of the outer tube is dependent upon the dimension of the inner tube. Because of this dependency, as the dimension of the inner tube increases so does the dimension of the outer tube. This relationship between the inner and outer tube influences the design selection and thus the performance characteristics of the catheter. Other factors may also affect the performance characteristics of the above-described catheters.

In addition, the manufacture of these catheters is not very flexible. For example, in a coaxial type catheter, the size of the outer tube must be selected and determined by the size of the inner tube as previously described. Thus, to construct such a catheter for a different size of guidewire both the inner and outer tubes must be changed. With reference to the dual or multiple lumen type catheter, a complete new extrusion must be performed to alter characteristics of the inflation and guidewire lumens.

It is desirable to provide an over-the-wire dilation catheter which overcomes the above-described limitations.

SUMMARY OF THE INVENTION

According to an aspect of the present invention an over-the-wire catheter and method of making such a catheter are provided, the catheter having a first tubular member defining a first lumen and a second tubular member defining a second lumen joined to and coextending with the exterior of the first tubular member to define a catheter shaft. The first and second tubular members are formed independently. A balloon is joined to the distal end of the catheter shaft where it is in fluid communication with the first lumen.

According to another aspect of the present invention an over-the-wire catheter and method of making such a catheter are provided the catheter having a first tubular member defining a first lumen and a second tubular member defining a second lumen joined to and coextending with the exterior of the first tubular member to define a catheter shaft. The first and second tubular members being formed of different materials. A balloon is joined to the distal end of the catheter shaft and is in fluid communication with the first lumen.

According to still another aspect of the present invention an over-the-wire catheter and method of making such a catheter are provided, the catheter having a first tubular member defining a first lumen a second tubular member defining a second lumen and a flexibility control member joined to and coextending with the exterior of the first and second tubular members to define a catheter shaft. A balloon is joined to the distal end of the catheter shaft and is in fluid communication with the first lumen.

BRIEF DESCRIPTION OF THE DRAWINGS

FIG. 1 is a longitudinal sectional view of an over-the-wire dilation catheter according to a preferred embodiment of the present invention.

FIG. 2 is a cross-sectional view taken along line A—A of the catheter of FIG. 1 according to a preferred embodiment of the present invention.

FIG. 3 is a cross-sectional view of the shaft of a catheter formed according to another preferred embodiment of the present invention.

FIG. 4 is a cross-sectional view of the relative positions of members used to form the shaft of a catheter according to a preferred embodiment of the present invention.

FIG. 5 is a cross-sectional view of the members shown in FIG. 4 enclosed in a heated die.

FIG. 6 is a longitudinal schematic of a flexibility control mender according to a preferred embodiment of the present invention.

FIG. 7 is a cross-sectional view taken along line 7—7 of the flexibility control member shown in FIG. 6.

FIG. 8 is a longitudinal sectional view of an over-the-wire dilation catheter according to another preferred embodiment of the present invention.

FIG. 9 is a cross-sectional view taken along line A—A of the catheter shown in FIG. 8 according to a preferred embodiment of the present invention.

FIG. 10 is a cross-sectional view of the shaft of a catheter according to another preferred embodiment of the present invention.

DETAILED DESCRIPTION OF THE PRESENTLY PREFERRED EMBODIMENTS

FIG. 1 illustrates a longitudinal sectional view of an over-the-wire dilation catheter 10 according to a first preferred embodiment of the present invention. Although the following description of the invention is directed to a balloon dilation catheter, it will be appreciated by those skilled in the art that the invention may be used on other interventional catheters with vascular interoperative devices, such as atherectomy devices, ultrasonic imaging and therapeutic catheters, laser catheters, stent delivery catheters and perfusion catheters.

The catheter 10 of FIG. 1 includes a shaft 12 having a proximal end and a distal end, a balloon 14 attached to a distal portion of the shaft 12 and a manifold 16 attached to the proximal end of the shaft 12. The terms proximal and distal are used to indicate relative locations along the catheter 10 with the distal end of the catheter 10 located at the right hand of FIG. 1 and the proximal end of the catheter located at the left hand of FIG. 1. The shaft 12 includes three separate and independent members, namely, a first tubular member 18 defining a first lumen 20, a second tubular member 22 defining a second lumen 24 and a flexibility control member 26. In a preferred embodiment, the first tubular member 18 has a proximal end and a distal end and a length of about 55 inches. In the proximal portion of the shaft 12 the first tubular member 18 has an outer diameter of about 0.0245 inches and an inner diameter of about 0.0185 inches. In the distal portion of the shaft 12 the first tubular member 18 is necked down to an outer diameter of about 0.0225 inches and an inner diameter of about 0.0165 inches. Reducing the diameter of a tubular member by necking is a well known technique known by those skilled in the art and thus need not be described in detail. While the first tubular member 18 is illustrated as having been necked down to a smaller diameter only once, there may of course be several such reductions.

The second tubular member 22 has a proximal end and a distal end, and in a preferred embodiment has been formed into an oval. The oval tubular member 22 has inner diameters of about 0.0120 inches and about 0.0170 inches at the points of millimum and maximum diameter respectively, wall thickness of about 0.0010 inches and a length of about 53.5 inches. The flexibility control member 26 is formed by a solid wire having a proximal end and a distal end. The wire has a diameter of about 0.0135 inches and a length of about 54 inches. In a preferred embodiment the distal portion of the wire is tapered no a diameter of about 0.0035 inches with an intermediate taper to a diameter of 0.007 inches to provide varying flexibility along the length of the shaft 12 as shown in FIG. 6. FIG. 7 is a cross-sectional view of the wire shown in FIG. 6 taken along lines 7—7. It will be appreciated by those skilled in the art that the dimensions of the catheter 10 may vary depending upon the size of the guidewire (not shown) used in conjunction therewith and the size of the balloon 14 attached thereto. The above dimensions are given as an example only and are not intended as a limitation. In another embodiment of the catheter which will be described in detail with reference to FIGS. 8–10, the flexibility control member 26 may be eliminated.

The first tubular member 18 may be formed of various materials depending upon the process used to join the three members of the shaft 12. If the three members of the shaft 12 are joined by a low temperature adhesive, the first tubular member 18 may be formed of polyethylene. If a hot melt adhesive is used to join the three members together, the first tubular member 18 may be formed of a material with a higher melt point such as Teflon or polyimide coated with Teflon on its inner diameter. Forming the first tubular member 18 of materials with good lubricity such as polyethylene, Teflon or Teflon coated polyimide provides good guidewire movement.

The second tubular member 22 is preferably formed of polyimide which allows it to have a wall thickness of about 0.001 inches or less. The flexibility control mender 26 is preferably formed of high tensile strength stainless steel. As previously described, the flexibility control member 26 provides varying flexibility along its length such that its flexibility increases in the distal direction. This may be accomplished by tapering the control member as shown in FIG. 6. This can be done using straight high tensile strength stainless steel wire. The wire is heat treated at a temperature ranging from about 700° F. to about 1000° F. to relieve stresses from straightening. Tapers then can be ground in the distal end of the wire using centerless grinding as is well known by those skilled in the art.

The construction of the catheter 10 of FIG. 1 will now be described in detail. The shaft 12 of catheter 10 is constructed by joining the three members together. More particularly, the three members are placed longitudinally adjacent to and substantially parallel with one another. Various methods may be used to join the three members together. A first preferred method will be described with reference to FIG. 2 which is a cross-sectional view taken along line A—A of the catheter 10 of FIG. 1. An adhesive 28 is applied to the three members along a substantial portion of the shaft 12 in which the three members are in contact with one another as can best be seen in FIG. 1. More particularly the adhesive 28 is applied from the proximal end of the shaft 12 to the distal ends of the second tubular member 22 and the flexibility control member 26 along one of the seams between the three members. Applying the adhesive in such a manner allows the adhesive to wick into and fill the gaps between the three members. In a preferred embodiment, a urethane adhesive, such as Urethane 3507 commercially available from the H.B. Fuller Company of St. Paul, Minn., is used. A die (not shown) can be wrapped around the three members at their proximal end to hold them in the correct position with respect to each other as the adhesive is applied. The die is advanced distally down the shaft as the adhesive is applied.

FIG. 3 is a cross-sectional view of the shaft of a catheter formed according to another preferred embodiment of the present invention. In this embodiment the three members are joined together by a sleeve 30 placed around the combined three members. The sleeve 30 may be heat shrunk onto the combined three members. The sleeve may be formed from a tube of a polyolefin copolymer (such as that sold by E.I. DuPont Nemours & Co. (Wilmington, Del.) under the tradename SURLYN as Resin No. 8527) irradiated with a 5 to 50 Megrad electroll beam and blow molded with a temperature of approximately 80° C. and a pressure of approximately 100 p.s.i. An adhesive 25 such as Urethane 3507 described above is then injected down the inside of the shrunk sleeve 30 to fill in any gaps between the three members. The sleeve 30 provides a smooth and continuous exterior surface to the catheter 10.

In another embodiment, the three members may be joined together by a molten material such as a hot melt adhesive. A cross-sectional view of the catheter shaft formed according to this embodiment would look substantially the same as the cross-sectional view shown in FIG. 2. FIG. 4 illustrates a cross-sectional view of the three members with the adhesive in the form of a strand 42 therebetween before heat is applied thereto. Preferably the strand 42 is a hot melt adhesive such as 3M 3748 from the 3M Corporation of St. Paul, Minn. More particularly, the three members are positioned longitudinally adjacent to one another and bonded no the manifold with solid strand 42 (approximately 0.006 inch diameter) of the hot melt adhesive bonded between the three members. The strand of adhesive 42 is cut so that it ends just proximal of the distal end of the second tubular member 22 so that it does not plug the second tubular member when the distal end of the strand of adhesive 42 melts. A two part heated die 44 as shown in FIG. 5 is then brought together around the menders just distal of the manifold. The die is heated to approximately 350°–400° F. and causes the strand 42 of hot melt adhesive to melt and flow to fill the gaps between the members. The die 44 is drawn down the length of the shaft, melting the adhesive as it passes. The first tubular member 18 in this embodiment must be formed of a heat resistant material such as Teflon or polyimide coated with Teflon on its inner diameter as previously described.

In still another embodiment of the present invention the three members of the shaft 12 may be joined by spray coating the members with a high durometer urethane dissolved into a solution with a solvent such as Dimethylacetamide.

In addition, the three members of the shaft may be releasably joined together. For example, short sleeve segments may be slid over portions of the three members or hoops may be provided on the exterior of one or more members, similar to the construction of a fishing pole, to allow the other member or members to slide therethrough.

FIG. 8 is a longitudinal sectional view of an over-the-wire dilation catheter according to another preferred embodiment of the present invention. The difference between the catheter shown in FIG. 8 and that shown in FIG. 1 is the elimination of flexibility control member 26. The same reference numerals have been used as were used in FIG. 1 to indicate similar elements. The first and second tubular members 18 and 22 may be joined together by the same methods described above with reference to the catheter of FIG. 1. FIGS. 9 and 10 illustrate cross-sectional views of the shaft of a catheter such as that shown in FIG. 8 joined by adhesives or a sleeve member. The dimensions described above with reference to the catheter of FIG. 1 apply equally to the catheter of FIG. 8.

The catheter shown in FIG. 8 may be provided with varying flexibility along its length in many ways such as necking the first tubular member 18 at various locations along the catheter shaft as shown or varying the amount of adhesive applied between the first and second tubular members 18 and 20 along the length of the catheter or applying a coating such as a high durometer urethane to a portion of the second tubular member 20 just to mention a few.

After the shaft 12 is formed by joining the three members, the balloon 14 is bonded to the distal portion of the shaft 12. The balloon 14 can be formed from a polyolefin copolymer or other polymer material. For example, in one embodiment, the balloon 14 is formed of a polyolefin copolymer (such as that sold by E.I. DuPont Nemours & Co. (Wilmington, Del.) under the tradename SURLYN as Resin No. 8527) using secondary treatment with 5 to 50 Mega-rad electron beam irradiation to enhance strength in the region of the balloon 14. The balloon 14 may be provided in a variety of conventional sizes suitable for PTCA use. In a preferred embodiment, the balloon 14 has a proximal waist 32 and a distal waist 34. The proximal waist 32 of the balloon 14 is placed over a portion of the first tubular member 18 and the distal end of the second tubular member 22 and the flexibility control member 26 which terminate proximal of the distal end of the first tubular member 18. The first tubular member 18 extends through the interior of the balloon 14 to the distal end of the catheter 10. The distal waist 34 of the balloon 14 is bonded to a distal portion of the first tubular mender 18. The proximal and distal waists 32 and 34 of the balloon 14 may be bonded by a urethane adhesive for example such as Urethane 3507 commercially available from the H.B. Fuller Co.

A radiopaque marker 36 may be placed around the first tubular member 18 in the interior of the balloon 14 to allow a physician to locate the catheter 10 while it is inserted within a patient's body as is well known by those skilled in the art.

A manifold 16 is connected to the proximal end of the shaft 12. Two separate luer fittings 38 and 40 provide access ports to the first and second tubular members 18 and 22 respectively. A source of inflation fluid (not shown) may be connected to the port formed by luer fitting 40 to provide inflation fluid to the second lumen 24 formed by the second tubular member 22. The inflation fluid is delivered to the interior of the balloon 14 through the open distal end of the second tubular member 22. The first lumen 20 formed by the first tubular member 18 defines a guidewire lumen. The port formed by luer fitting 38 allows a guidewire (not shown) to extend therethrough. Of course those skilled in the art will appreciate that other types of manifolds may be used with the shaft 12 so that inflation fluid is delivered to the interior of the balloon 14 through the second lumen and a guidewire has access to the first lumen 20.

As those skilled in the art will appreciate a strain relief member (not shown) may be placed around the joined members of the shaft just distal of the manifold. The strain relief member may be a tube formed of SURLYN having a length of about 1.0 inch.

The catheter 10 of the present invention is designed for use in combination with a catheter guide element such as a guidewire (not shown). In use in a coronary application, both the guidewire and the catheter 10 are fed through and guided to an arterial lesion by means of a tubular guide catheter (not shown) as is well known by those skilled in the art and thus need not be described in further detail.

An advantage of the over-the-wire dilation catheter according to a preferred embodiment of the present invention is one ability to select the desired performance characteristics of the catheter by the selection of individual components. The inflation lumen, guidewire lumen and flexibility control member are independent so that the size and material of one lumen can be selected without affecting the size and material of the other. In addition, another advantage is a catheter having a simple construction which offers flexibility in designing and manufacturing the catheter to suit a particular environment. More particularly it is an advantage to provide a catheter in which each component including the inflation and guidewire lumens is formed as a basic building block of the catheter. These building blocks may come in various materials, sizes and dimensions which can be assembled in different combinations to allow the manufacturer to produce catheters with a number of functional differences from a relatively small number of different components. It is also an advantage to provide an over-the-wire dilation catheter having a smooth transition in flexibility along its length.

In addition, forming the inflation lumen from a polyimide tube creates a very thin walled second tubular member 22 preferably having a wall thickness on the order of about 0.001 inches or less. This allows the profile of the catheter 10 to be kept to a minimum even when the size of the guidewire lumen is increased. In addition, it allows the guidewire lumen to be formed of materials that provide good guidewire movement while still maintaining the Low profile of the catheter.

As a result of the simplified construction of the catheter 10 the dimension and material of each component may be selected simply and efficiently.

While the invention has been shown and described in connection with particular preferred embodiments, it is apparent that certain changes and modifications, in addition to those mentioned above, may be made by those who are skilled in the art without departing from the basic features of the present invention. Accordingly, it is the intention of the Applicants to protect all variations and modifications within the true spirit and valid scope of the invention.

What is claimed is:

1. An-over-the wire catheter comprising:
   (a) a first tubular member defining a first lumen;
   (b) a second tubular member defining a second lumen;
   (c) said first and second tubular members having exterior surfaces in contact with each other over a substantial length thereof in a non-coaxial manner;
   (d) a flexibility control member co-extending with and exterior to both the first and second tubular members, the flexibility control member joined to at least one of the first and second tubular members along a portion of their longitudinal length to define a catheter shaft; and
   (e) a balloon joined to the distal end of the catheter shaft and in fluid communication with the first lumen.

2. An over-the-wire catheter according to claim 1 wherein the flexibility control member comprises a wire.

3. An over-the-wire catheter according to claim 1 wherein the flexibility control member is tapered to a smaller diameter at its distal end.

4. An over-the-wire catheter according to claim 1 wherein the distal end of the flexibility control member is proximal to the distal end of the second tubular member.

5. An over-the-wire catheter according to claim 1 wherein the distal end of the flexibility control member terminates under the balloon.

6. An over-the-wire catheter, comprising:
   (a) a first tubular member defining a first lumen;
   (b) a second tubular member defining a second lumen;
   (c) the exterior of the second tubular member joined to and co-extending with the exterior of the first tubular member to define a catheter shaft;
   (d) a balloon joined to the distal end of the catheter shaft and in fluid communication with the first lumen, wherein said first and second tubular members are formed independently; and
   (e) means for varying the flexibility of at least one of the first and second tubular members.

7. An over-the-wire catheter, comprising:
   (a) a first tubular member defining a first lumen;
   (b) a second tubular member defining a second lumen;
   (c) the exterior of the second tubular member joined to and co-extending with the exterior of the first tubular member to define a catheter shaft;
   (d) a balloon joined to the distal end of the catheter shaft and in fluid communication with the first lumen, wherein said first and second tubular members are formed independently; and
   (e) wherein the first and second tubular members are joined together by an adhesive.

8. An over-the-wire catheter, comprising:
   (a) a first tubular member defining a first lumen;
   (b) a second tubular member defining a second lumen;
   (c) the exterior of the second tubular member joined to and co-extending with the exterior of the first tubular member to define a catheter shaft;
   (d) a balloon joined to the distal end of the catheter shaft and in fluid communication with the first lumen, wherein said first and second tubular members are formed independently; and
   (e) wherein the first and second tubular members are joined together by a sleeve member.

9. An over-the-wire catheter, comprising:
(a) a first tubular member defining a first lumen;
(b) a second tubular member defining a second lumen;
(c) the exterior of the second tubular member joined to and coextending with the exterior of the first tubular member to define a catheter shaft;
(d) a balloon joined to the distal end of the catheter shaft and in fluid communication with the first lumen, wherein said first and second tubular members are formed independently; and
(e) wherein the first and second tubular members are releaseably joined together.

10. An over-the-wire catheter comprising:
(a) a first tubular member defining a first lumen;
(b) a second tubular member defining a second lumen;
(c) the exterior of the second tubular member joined to and substantially coextending with the exterior of the first tubular member in a non-coaxial manner to define a catheter shaft;
(d) a balloon joined to the distal end of the catheter shaft and in fluid communication with the first lumen, wherein said first and second tubular members are formed of different materials; and
(e) means for varying the flexibility of at least one of the first and second tubular members.

11. A method of making an over-the-wire catheter comprising the steps of:
(a) forming a first tubular member having a proximal end and a distal end, the first tubular member defining an inflation lumen;
(b) forming a second tubular member having a proximal end and a distal end, the second tubular member defining a guide wire lumen wherein the second tubular member is formed separately and independently from the first tubular member;
(c) joining the exterior of the first and the exterior of the second tubular members together to form a catheter shaft having a proximal end and a distal end, the step of joining the first and second tubular members including heat-shrinking a sleeve member over the first and second tubular members; and
(d) attaching a balloon member to the shaft near its distal end.

12. A method of making an over-the-wire catheter comprising the steps of:
(a) forming a first tubular member having a proximal end and a distal end, the first tubular member defining an inflation lumen;
(b) forming a second tubular member having a proximal end and a distal end, the second tubular member defining a guide wire lumen wherein the second tubular member is formed separately and independently from the first tubular member;
(c) joining the exterior of the first and the exterior of the second tubular members together to form a catheter shaft having a proximal end and a distal end, the step of joining the first and second tubular members including applying an adhesive around the members; and
(d) attaching a balloon member to the shaft near its distal end.

13. A method of making an over-the-wire catheter comprising the steps of:
(a) forming a first tubular member having a proximal end and a distal end, the first tubular member defining an inflation lumen;
(b) forming a second tubular member having a proximal end and a distal end, the second tubular member defining a guide wire lumen;
(c) providing a flexibility control member;
(d) joining the exterior of the first and the exterior of the second tubular members together to form a catheter shaft having a proximal end and a distal end;
(e) joining a flexibility control member to the exterior of the shaft formed by the first and second tubular members so that the flexibility control member coextends with the shaft; and
(f) attaching a balloon member to the shaft near its distal end.

* * * * *